United States Patent [19]

Boenning et al.

[11] Patent Number: 5,150,603
[45] Date of Patent: Sep. 29, 1992

[54] HYDROCARBON VAPOR SENSOR AND SYSTEM

[75] Inventors: Robert A. Boenning, Timonium; David L. Blair, Cockeysville, both of Md.

[73] Assignee: Westinghouse Electric Corp., Pittsburgh, Pa.

[21] Appl. No.: 819,896

[22] Filed: Dec. 13, 1991

[51] Int. Cl.$^5$ .................... G01N 27/12; G01M 3/16
[52] U.S. Cl. .................................................. 73/31.05
[58] Field of Search ............. 73/31.05, 23.4, 49.2

[56] References Cited

U.S. PATENT DOCUMENTS

| | | | |
|---|---|---|---|
| 2,930,015 | 3/1960 | Blumer | 73/31.05 X |
| 3,045,198 | 7/1962 | Dolan et al. | 73/73 X |
| 3,999,122 | 12/1976 | Winstel et al. | 73/31.06 X |
| 4,236,307 | 12/1980 | Colla et al. | 338/34 X |
| 4,387,359 | 6/1983 | Tien et al. | 338/34 |
| 4,631,952 | 12/1986 | Donaghey | 73/31.05 X |
| 4,633,704 | 1/1987 | Tantram et al. | 73/31.05 |
| 4,674,320 | 6/1987 | Hirschfeld | 73/31.06 |
| 4,745,796 | 5/1988 | Abdelrahman et al. | 73/31.05 X |
| 4,928,513 | 5/1990 | Sugihara et al. | 73/31.06 X |

Primary Examiner—Hezron E. Williams
Assistant Examiner—Joseph W. Roskos
Attorney, Agent, or Firm—John K. Williamson; Norman A. Nixon

[57] ABSTRACT

A hydrocarbon vapor sensor which is simple and low cost and can easily detect the existence of hydrocarbon vapor. The device is temperature compensated so that a change in resistance due to a change in temperature is avoided and an accurate response is always provided. The sensor can be used in a system in which a number of sensors are provided at various depths to determine whether a leak or a ground spill has occurred.

7 Claims, 6 Drawing Sheets

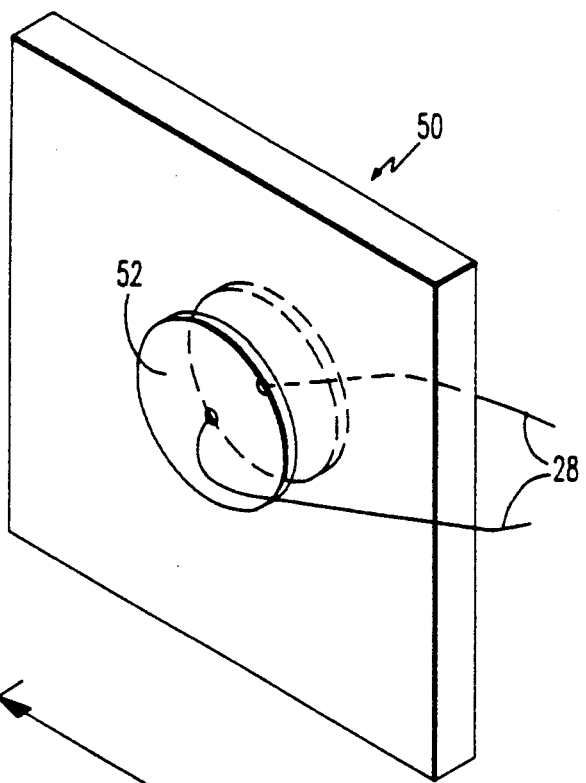
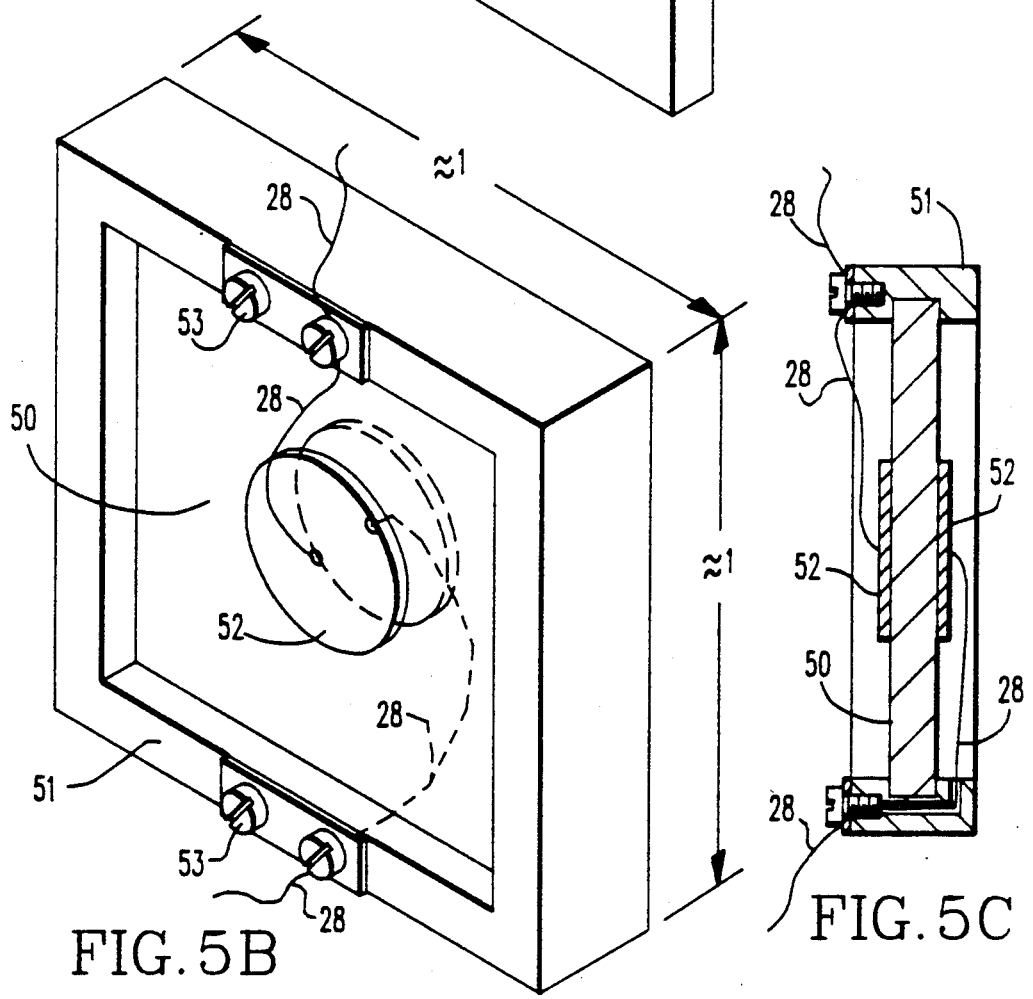
FIG. 5A
FIG. 5B
FIG. 5C

HYDROCARBON VAPOR SENSOR AND SYSTEM

BACKGROUND OF THE INVENTION

1. Field of the invention

The present invention is directed to a simple low cost hydrocarbon vapor sensor and system employing the same. The sensor is used, for example, for detecting hydrocarbon leaks in buried fuel storage tanks. The vapor sensor can employ carbon-filled ethylene propylene rubber (EPR) semiconductive tape as a sensing element or a normally closed switching elastomer that opens when hydrocarbon vapor is adsorbed.

2. Description of the Related Art

Monitoring fuel storage tanks, particularly those underground, for hydrocarbon leaks is an exceedingly important environmental concern. Current detection/monitoring systems for monitoring leaks in fuel storage tanks can employ, for example, semiconductor, capacitive, and conductive liquid crystalline sensors or gas analyzers for detecting liquid or vapor leaks. These systems are complicated and very expensive.

Electrically conductive polymeric materials, such as conductive rubber, have been used for detecting liquid hydrocarbons, but must be placed at locations such as a sump where leaking liquid will collect and directly contact the sensor.

U.S. Pat. No. 4,631,952 to Donaghey, teaches a prior art device that employs a resistive sensing element which is sensitive to vapor as well as liquid. The sensing element includes an admixture of a swellable matrix and conductive particles, such as synthetic rubber, polyvinyl chloride, silicone rubber and finely divided carbon. Silicone rubber is preferred. The sensor is sensitive to five parts per million (ppm) of hydrocarbon vapor. This sensor, however, does not provide for temperature compensation. Therefore, unless it is in an environment in which the temperature is constant, resistance changes due to even small temperature changes will exceed those due to vapor concentration. Consequently, devices such as those taught by Donaghey are not practical.

Another prior art sensor is a silicone polymer sensor. Such sensors conduct electricity but are not affected by water. The sensor is sensitive to liquid hydrocarbon. The sensor has a low resistance and has a high density of carbon black particles. This type of sensor is not responsive to gas-phase hydrocarbons.

Additional prior art sensors include combustion energy, flame ionization, gas chromatography, chemical, absorption force, and optical sensors. These sensors are all expensive, complicated and are not suitable for detecting hydrocarbon leaks.

SUMMARY OF THE INVENTION

An object of the present invention is to provide a simple low-cost hydrocarbon vapor sensor that is highly sensitive and quickly responds to small amounts of hydrocarbon vapor.

Another object of the present invention is to provide a hydrocarbon vapor sensor which is insensitive to temperature changes.

Yet another object of the present invention is to provide a reusable hydrocarbon vapor sensor.

Another object of the present invention is to provide a system of hydrocarbon vapor sensors to detect whether hydrocarbon vapor is from an actual leak in a storage tank or whether it is from an above ground spill.

To achieve the above-mentioned and other objects, the present invention provides a hydrocarbon vapor sensor including a first sensing means stretched between two clamps on a first side of an I-beam shaped member and a second sensing means stretched between two clamps on a second side of the I-beam shaped member. The first sensing means is covered with a perforated cover and the second sensing means is covered with a sealed cover. The second sensing means provides temperature compensation. The first and second sensing means can include, for example, ethylene propylene rubber or the elastomeric matrixes containing carbon particles.

One or more hydrocarbon vapor sensors can be provided in a system. The sensor located furthest from the surface detects a leak when its resistance is greater than the resistance of any of the sensors located closer to the surface. A surface spill is detected when the sensors closest to the surface have a resistance greater than the sensors furthest from the surface.

These objects, together with other objects and advantages, which will be subsequently apparent, reside in the details of construction and operation as more fully hereinafter described and claimed, reference being had to the accompanying drawings forming a part hereof, wherein like reference numerals refer to like parts throughout.

BRIEF DESCRIPTION OF THE DRAWINGS

FIGS. 5A, 5B and 5C are schematic diagrams of a second embodiment of a hydrocarbon vapor sensor according to the present invention;

DESCRIPTION OF THE PREFERRED EMBODIMENTS

Figure 1:
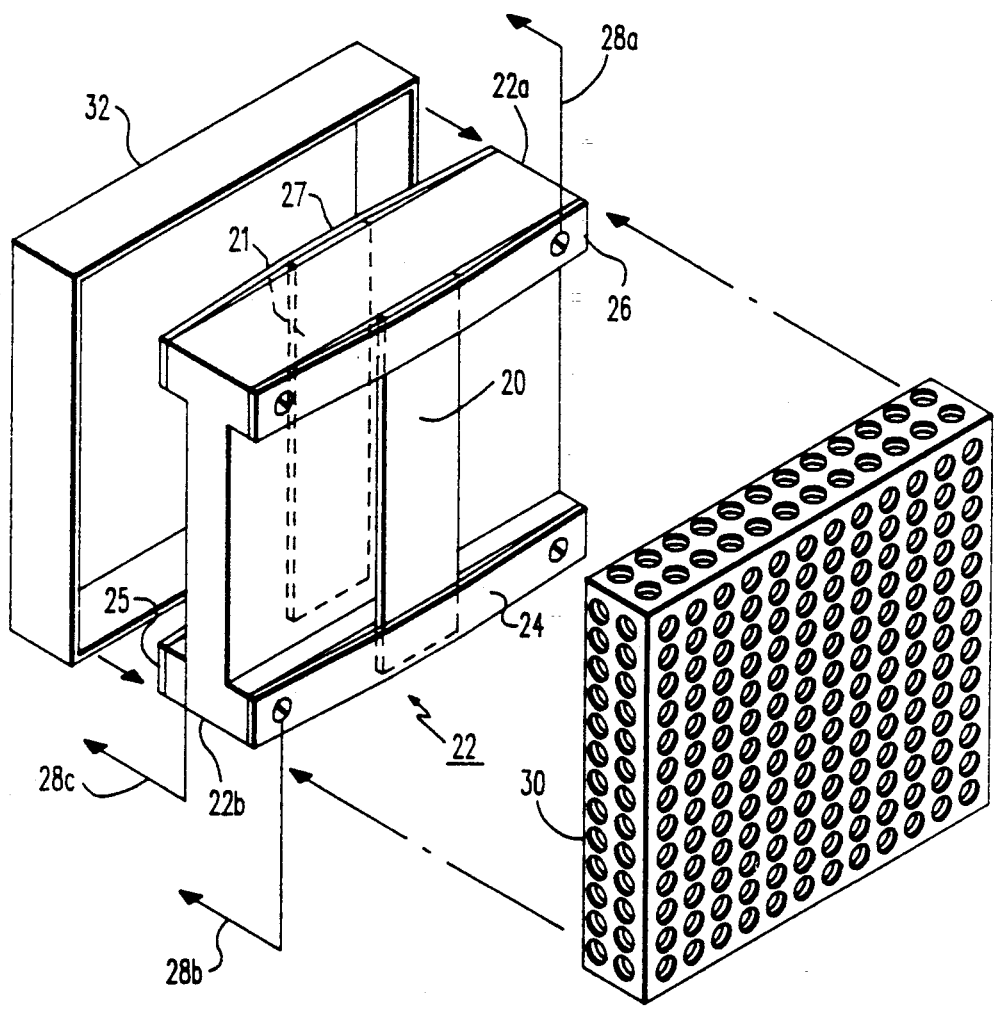
FIG. 1 is an exploded perspective view of a first embodiment of a hydrocarbon vapor sensor according to the present invention.

FIG. 1 is an exploded perspective view of a first embodiment according to the present invention. In FIG. 1, an ethylene propylene rubber (EPR) tape 20 includes carbon particles and is used as a sensor. In a preferred embodiment, the tape 20 can comprise, for example, Scotch no. 13 electrical semiconducting tape, manufactured by 3M. This tape is nonvulcanizing and shelf stable and remains flexible over a wide temperature range. Although the vapor sensing tape 20 is normally manufactured for covering high voltage splices to prevent corona, the inventor discovered that it makes an ideal hydrocarbon vapor (and liquid) sensor. The vapor sensing tape 20 also has exceptional resistance to cracking or checking from solvents, UV or moisture. The tape has a high resistance of approximately 8.5 kΩ per inch in a relaxed state. When stretched, the resistance is reduced to approximately 2.6 kΩ per inch at a width of three-eighth inches. The thickness when stretched is approximately 0.015 inches thick.

It is well known that carbon exhibits a pressure sensitive resistance characteristic. That is, when pressure increases, resistance decreases. The resistance of the vapor sensing tape 20 increases because pressure between carbon particles in the rubber matrix is reduced when the rubber expands when exposed to hydrocarbon vapor. This mechanism has been found to be reversible. As a result, when the tape is removed from hydrocarbon vapor, the vapor sensing tape 20 returns to its initial resistance after the adsorbed hydrocarbon has evaporated.

The inventor has discovered that when the vapor sensing tape 20 in the present invention is stretched it adsorbs hydrocarbon vapor faster and at lower concentrations. The vapor sensing tape 20 is stretched and annealed at room temperature for approximately twelve hours or by a hot air gun for approximately 15 minutes. This annealing allows the tape to obtain a constant resistance value.

The vapor sensing tape 20 is placed on, for example, an acrylic I-beam member 22 as shown in FIG. 1. The vapor sensing tape 20 is stretched and clamped between two ends 22a and 22b on one side of the I-beam member 22 with metal clamps 24 and 26. Since there is an air space between the I-beam member 22 and the stretched vapor sensing tape 20, a greater area of the vapor sensing tape 20 is exposed. The vapor sensing tape 20 is therefore more sensitive and responds more quickly than if there was no air space.

A temperature sensing tape 21 is located on the I-beam member 22 opposite the vapor sensing tape 20. The temperature sensing tape 21 is stretched and clamped to the I-beam member 22 with metal clamps 25 and 27. The temperature sensing tape 21 has the same characteristics, dimensions and resistance as the vapor sensing tape 20.

An end 22a of the vapor sensing tape 20 and an end of the temperature sensing tape 21 are commonly connected to a wire lead 28a as shown in FIG. 1. End 22b of the vapor sensing tape 20 is connected to a wire lead 28b. End 22b of the vapor sensing tape 21 is connected to a wire lead 28c.

A perforated cover 30 covers the vapor sensing tape 20 on the first side of the I-beam member 22. A solid cover 32 hermetically seals the temperature sensing tape 21 on the second side of the I-beam member 22. This allows both the vapor sensing tape 20 and the temperature sensing tape 21 to "see" the same temperature. Only the vapor sensing tape 20, however, is exposed to hydrocarbon vapor.

Figure 2:
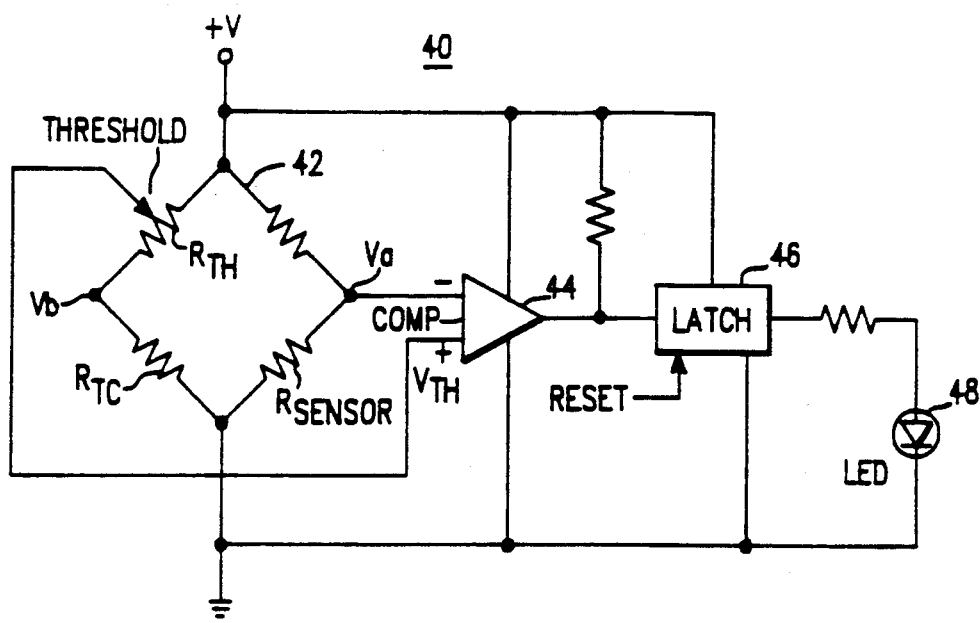
FIG. 2 is a schematic diagram of vapor sensing circuit employing a bridge circuit for achieving temperature compensation in conjunction with the hydrocarbon vapor sensor in FIG. 1.

FIG. 2 is a schematic diagram of a vapor sensing circuit employing a bridge circuit 42 for achieving temperature compensation in conjunction with the hydrocarbon vapor sensor of FIG. 1. The vapor sensing tape 20 and the temperature sensing tape 21 are schematically represented as adjacent legs in the bridge circuit 42 to provide temperature compensation. The vapor sensing tape 20 corresponds to $R_{SENSOR}$ and the temperature sensing tape 21 corresponds to $R_{TC}$. The threshold potentiometer resistor $R_{TH}$ and the remaining resistor R have the same values as $R_{SENSOR}$ and $R_{TC}$.

The circuit 40 includes a comparator 44, a latch 46, and an indicator LED 48. These circuits are well known. The threshold potentiometer $R_{TH}$ determines when the output from the comparator 44 falls to a low voltage level; that is, at what voltage $V_a$ becomes more positive than $V_{TH}$. The low voltage output from the comparator 44 sets the latch 46 and turns the indicator LED 48 ON. The threshold voltage $V_{TH}$ is established by $V_a$. The voltage $V_a$ is determined by the resistance of $R_{SENSOR}$ when it is exposed to a predetermined hydrocarbon vapor concentration of, for example, 600 parts per million (ppm).

Temperature compensation is accomplished by the bridge circuit 42 in accordance with the following equation:

$$R_{SENSOR} \cdot R_{TH} = R_{TC} \cdot R \qquad (1)$$

when $V_a = V_b$ and $V_{TH} - C_a = k$, where k is a constant. The resistances $R_{TH}$ and R are constant with temperature and $\Delta R_{SENSOR} = \Delta R_{TC}$ as temperature changes. Therefore, $V_a$ will equal $V_b$ over a specified temperature range when $R_{SENSOR}$ is not exposed to hydrocarbon vapor. Consequently, any increase in $V_a$ with respect to $V_{TH}$ is due to an increase in $R_{SENSOR}$ resulting from adsorption of hydrocarbon vapor.

The analog circuit in FIG. 2 can be digitally implemented using a microprocessor. The microprocessor can provide a digital readout in ppm vapor concentration for more than one sensor, can provide a display of a previous reading, and can have a built-in self test to determine if the digital apparatus is functioning properly.

Figure 3:
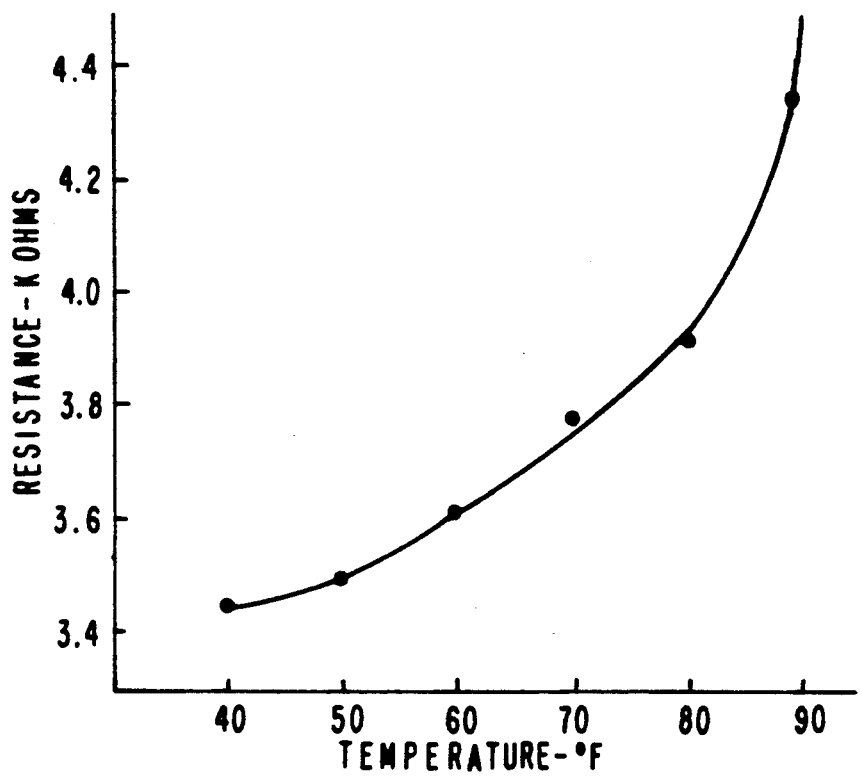
FIG. 3 is a graph of temperature versus resistance characteristics of a hydrocarbon vapor sensor such as shown in FIG. 1.

Temperature compensation is very important since the resistance of the EPR tape 20 (and similar filled elastomer materials) is adversely affected by temperature as shown in FIG. 3. FIG. 3 is a graph of temperature in degrees Fahrenheit versus resistance in kΩ of the vapor sensing tape 20. Between temperatures of 40° and 90° F., the resistance of the described sensor increases from approximately 3.5 kα to 4.35 kΩ. Therefore, a sensor that is not temperature compensated is likely to give a false reading that a leak is present if the temperature changes. The sensor may also become desensitized so that a leak is never registered. The ambient temperature of a sensor can change, for example, due to filling a storage tank in hot summer weather or cool winter weather. This would affect the temperature of the hydrocarbon, such as gasoline, being input from an external tank to an underground tank.

Figure 4:
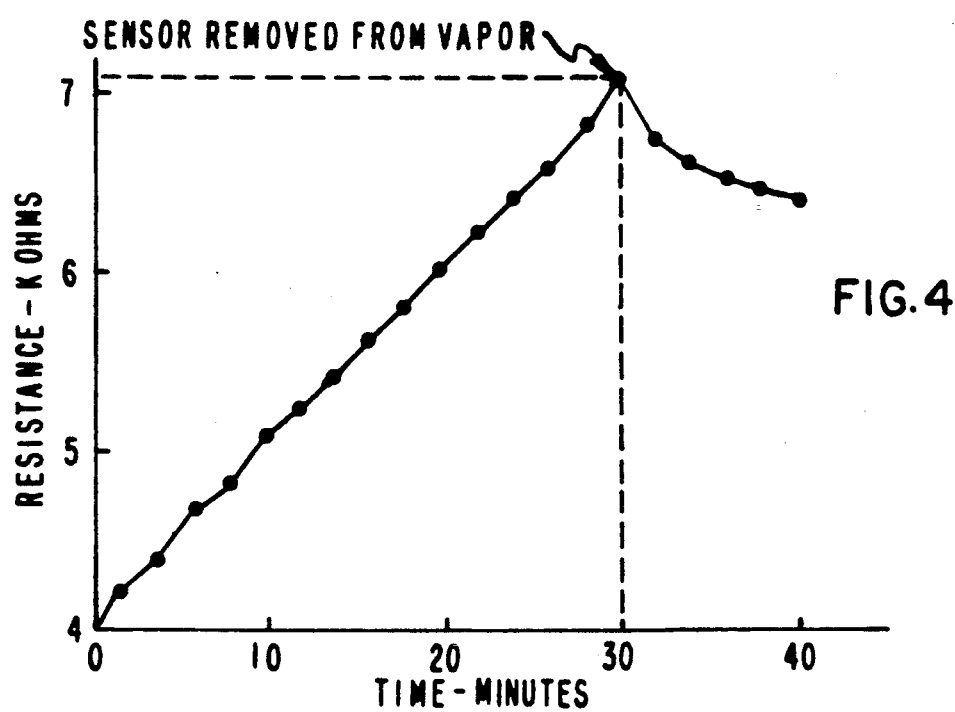
FIG. 4 is a graph of time versus resistance characteristics of a hydrocarbon vapor sensor such as shown in FIG. 1.

FIG. 4 is a graph of the resistance versus time response (under essentially constant temperature) in an atmosphere having a high concentration of hydrocarbon vapor, e.g., approximately 4000 ppm. This graph indicates that the sensor of the present invention responds quickly to hydrocarbon vapor.

A second embodiment according to the present invention is shown in FIGS. 5A–5C. The hydrocarbon vapor sensor in this embodiment includes a switching material 50. The hydrocarbon sensor 50 exploits the switching characteristics of a material developed for detecting cable pinching. The material includes an EPR elastomer, or silicon rubber, filled with conducting particles to a critical density. The conducting particles include a volume concentration of, for example, 10 micron diameter silver-coated glass spheres or metallic silver flake, in an elastomeric matrix. Contacts 52 are connected to either side of the material.

FIG. 5B is a perspective view of a hydrocarbon vapor sensor 50 mounted to a sensor mount 51. The ends of the contacts 52 are connected to the ends of the sensor mount 51. Wire leads 28 are connected to terminals 53 on both sides of the sensor mount 51. Temperature compensation, however, is not necessary since the switching material is not highly sensitive to temperature. FIG. 5C is a side view of the mounted hydrocarbon vapor sensor 50 shown in FIG. 5B.

Figure 6:
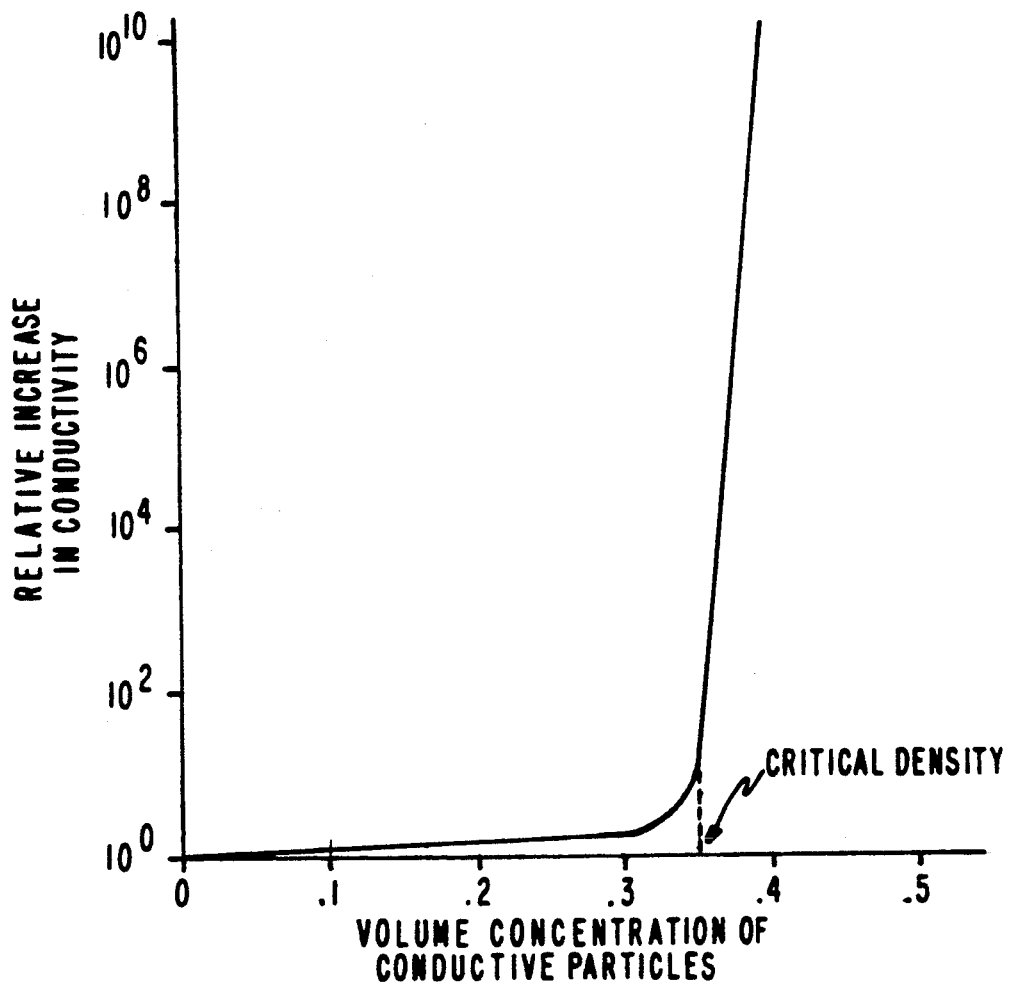
FIG. 6 is a graph of the volume concentration of conductive particles versus conductivity for the hydrocarbon vapor sensor such as shown in FIG. 5A.

The elastomeric material in the hydrocarbon vapor sensor 50 becomes conductive when the volume concentration of the spheres or flakes in the elastomeric matrix exceeds a critical density. The critical density is determined when the elastomer is filled to approximately 33% to 34%, e.g., just until the material conducts, as shown by the graph in FIG. 6. Exposure to hydrocarbon vapor or liquid will cause the elastomer to expand, reducing the volume concentration of the conducting particles below the critical density necessary for conduction. The material becomes non-conductive at a specific hydrocarbon exposure level. As the material expands due to adsorption of hydrocarbon vapor, a conductive path between the two contacts 52 opens and provides a signal to operate a detection circuit 60 shown in FIG. 7. As shown in FIG. 6, when the elastomer reaches the critical density, the material will exhibit volume conduction that is normally ON (conductive). The hydrocarbon level at which switching takes place can be established by controlling the thickness and elasticity of the elastomeric matrix.

Figure 7:
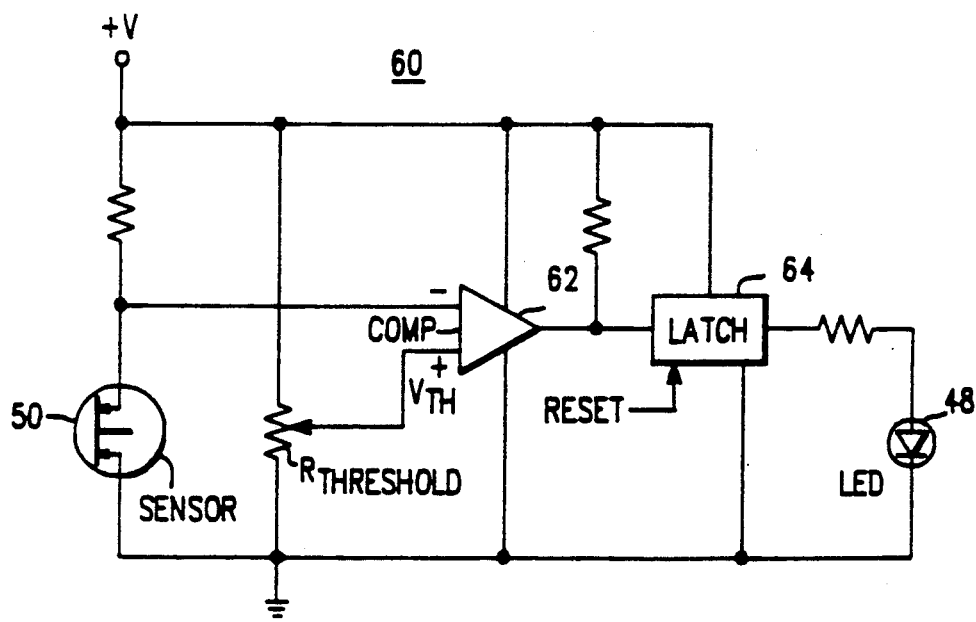
FIG. 7 is a schematic diagram of a detection circuit used with the hydrocarbon vapor sensor such as shown in FIG. 5A.

The circuit shown in FIG. 7 detects when the sensor 50 is open, e.g., not conducting. The detection circuit 60 includes a comparator 62 which receives the output from the hydrocarbon vapor sensor 50, an adjustable threshold resistor $R_{TH}$, and a latch circuit 64. The output from the latch circuit 64 drives a display 48. As is well known, the sensitivity of switching material can be controlled by tailoring the properties of the elastomer and the dimensions of the sensor 50. The sensor 50 is also appropriate for sensing hydrocarbon liquid and is not affected by water.

Figure 8B:
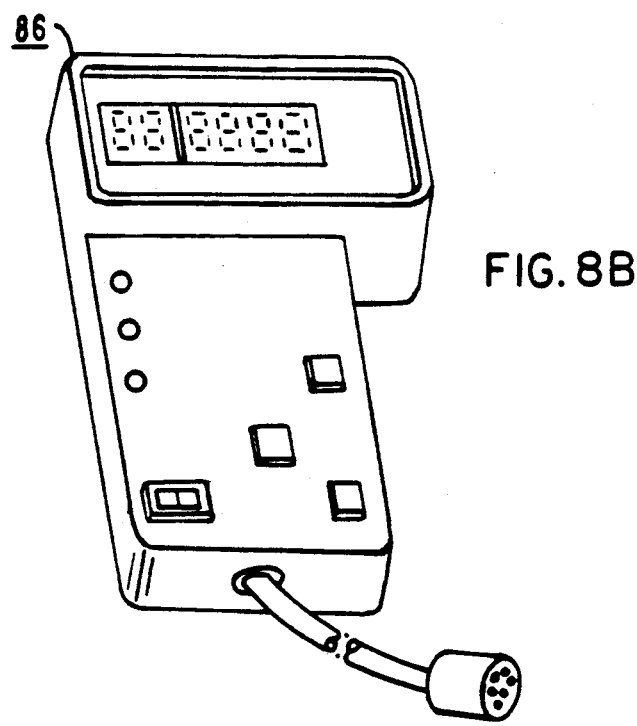
FIG. 8B is a perspective view of a microprocessor controlled unit connectable to the system as shown in FIG. 8A.
Figure 8A:
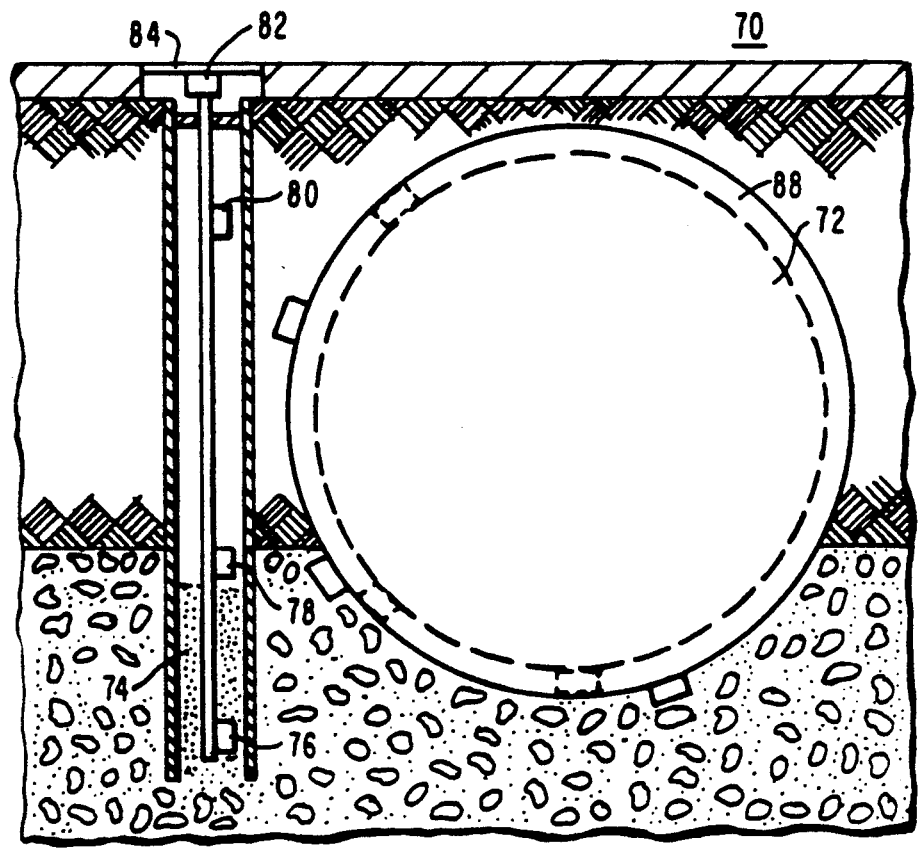
FIG. 8A is a schematic diagram of a system which employs a plurality of hydrocarbon vapor sensors to detect a leak in an underground storage tank.

FIG. 8A is a diagram of a hydrocarbon vapor sensor system. This system includes a plurality of hydrocarbon vapor sensors arranged to distinguish between a leak in an underground tank 72 and a ground spill. A first sensor 76 can be placed at a lowermost portion of the vapor well 74 which is adjacent to the underground tank 72 and at a position lower than the underground tank 72. The first sensor 76 detects leaks from the underground tank 72 since it is the bottom portion of the tank in which leaks are most likely to occur. Also, hydrocarbon vapor is heavier than air and will settle to a lowest point.

A second sensor 78 is located at some position above the first sensor 76. Preferably, the second sensor 78 is placed at an area where the ground and gravel fill, on which the underground tank 72 rests, meet. The second sensor 78 can also detect tank leaks but may also detect a ground spill if the ground spill is large enough.

A third sensor 80 is located at a position above the second sensor near the surface. The third sensor 80 detects ground spills. A connector 82 is located above the third sensor 80 and is covered with a cover plate 84. The connector 82 allows a microprocessor controlled hand-held unit 86 (FIG. 8B) to be connected to the three (or more) sensors and can determine whether a leak is an actual leak or a ground spill. The microprocessor controlled unit 86 measures the resistance of each of the sensors and performs a comparison operation. If a resistance $R_1$ of the first sensor 76 is greater than a resistance $R_2$ of the second sensor 78, and the resistance $R_2$ of the second sensor 78 is greater than a resistance $R_3$ of the third sensor 80, then the probability is high that a leak is detected. If the resistance $R_1$ is less than the resistance $R_2$ and the resistance $R_2$ is less than the resistance $R_3$, then a spill is detected. It should be noted that any number of sensors can be used in a vapor well. To determine that a leak exists, the resistance $R_1$ of the first sensor (the sensor furthest from the surface) must be greater than the other sensors.

The microprocessor controlled unit 86 can: display readouts for the resistances of the sensors; can display the amount of hydrocarbon vapor in parts per million detected by each sensor; can store and provide a read out of a previous resistance reading of each sensor; can detect whether a sensor is bad; and can perform a self check. Other additional functions can be provided depending on the system.

More than one vapor well 74 can be provided. That is, at least six vapor wells, including at least three sensors per vapor well, would provide an accurate reading for any leaks in an underground storage tank 72. Two sensors, for example, would be located along each long side of the tank and one sensor would be located at each end.

The sensors do not necessarily have to be placed in vapor wells 74. They can be placed, for example, in an interstitial area 88 surrounding the storage tank 72, as shown by the dotted line in FIG. 8. In addition, they can be placed at various positions external to the storage tank 72 as shown by the dark boxes on the exterior of the storage tank 72.

Although the present invention has been described as being used in air or underground, it can also be applied to a water environment to determine contamination by a hydrocarbon. The sensors, and wirings, however, must be insulated.

As noted above, the present invention provides a hydrocarbon sensor which can inexpensively and easily detect the existence of hydrocarbon vapor. The response time of the device is very quick and it is not susceptible to temperature variations so that an accurate response is always provided.

The foregoing is considered as illustrative only of the principles of the invention. Further, since numerous modifications and changes will readily occur to those skilled in the art, it is not desired to limit the invention to the exact construction and application shown and described, and accordingly, all suitable modifications and equivalents may be resorted to, falling within the scope of the invention and the appended claims and their equivalents.

What is claimed is:
1. A hydrocarbon vapor sensor, comprising:
 a sensor mount having members for supporting an elastomeric material on all edges;
 an elastomeric matrix mounted to said sensor mount having a resistance responsive to hydrocarbon vapor and including metal coated glass spheres;

comparator means for receiving a voltage when said elastomeric matrix senses hydrocarbon vapor, for comparing said voltage with a predetermined threshold voltage and for outputting a signal;

latch means for outputting a signal indicating hydrocarbon vapor has been sensed in accordance with the output signal from said comparator means; and display means for providing a readout indicative of the sensed hydrocarbon vapor.

2. A hydrocarbon vapor sensor system having an underground storage tank, said hydrocarbon sensor system comprising:

first hydrocarbon vapor sensor means located near a bottom portion of the storage tank, for sensing hydrocarbon vapor;

second hydrocarbon vapor sensor means located near a portion of the storage tank between a top portion of the storage tank and the bottom portion of the storage tank, for sensing hydrocarbon vapor;

third hydrocarbon vapor sensor means located near the top portion of the storage tank, for sensing hydrocarbon vapor near the top portion of the sensing tank;

means connectable at the top portion of the storage tank, for determining a leak when a resistance of said first hydrocarbon vapor sensor means is greater than a resistance of said second hydrocarbon vapor sensor means and the resistance of said second hydrocarbon vapor sensor means is greater than a resistance of said third hydrocarbon vapor sensor means and for determining a spill when the resistance of said first hydrocarbon vapor sensor means is less than the resistance of said second hydrocarbon vapor sensor means which is less than the output from said third hydrocarbon vapor sensor means; wherein each of said first through third sensing means comprises:

a sensor mount having members for supporting an elastomeric material on all edges;

an elastomeric matrix mounted on said vapor sensor mount having a resistance responsive to hydrocarbon vapor and including metal coated glass spheres.

3. A hydrocarbon vapor sensor system according to claim 2, wherein when said metal coated glass spheres are exposed to hydrocarbon vapor the resistance of said elastomeric matrix increases.

4. A hydrocarbon vapor sensor system according to claim 2, wherein said hydrocarbon vapor sensor means are located in a space between an inner portion of the storage tank and an outer portion of the storage tank.

5. A hydrocarbon vapor sensor system according to claim 2, wherein said first, second and third hydrocarbon vapor senor means are located exterior to the storage tank.

6. A hydrocarbon vapor sensor system according to claim 2, wherein said first through third hydrocarbon vapor sensor means are located in a vapor well adjacent the storage tank.

7. A hydrocarbon vapor sensor system according to claim 2, comprising more than three hydrocarbon vapor sensors.

* * * * *